(12) United States Patent
Auricchio et al.

(10) Patent No.: US 7,676,259 B2
(45) Date of Patent: *Mar. 9, 2010

(54) DYNAMICALLY OPTIMIZED MULTISITE CARDIAC RESYNCHRONIZATION DEVICE

(75) Inventors: Angelo Auricchio, Magdeburg (DE); Julio C. Spinelli, Shoreview, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 787 days.

This patent is subject to a terminal disclaimer.

(21) Appl. No.: 11/135,191

(22) Filed: May 23, 2005

(65) Prior Publication Data
US 2005/0216066 A1    Sep. 29, 2005

Related U.S. Application Data

(63) Continuation of application No. 10/071,875, filed on Feb. 8, 2002, now Pat. No. 6,915,160.

(51) Int. Cl.
*A61B 5/04* (2006.01)
(52) U.S. Cl. ..................................... 600/509
(58) Field of Classification Search .............. 607/4, 607/5, 9, 17, 28; 600/509, 521, 517, 516
See application file for complete search history.

(56) References Cited

U.S. PATENT DOCUMENTS

| | | | |
|---|---|---|---|
| 3,606,882 A * | 9/1971 | Abe et al. ............. | 600/516 |
| 4,354,497 A | 10/1982 | Kahn | |
| 4,549,548 A | 10/1985 | Wittkampf et al. | |
| 4,554,922 A | 11/1985 | Prystowsky et al. | |
| 4,628,934 A | 12/1986 | Pohndorf et al. | |
| 4,674,518 A | 6/1987 | Salo | |
| 4,686,987 A | 8/1987 | Salo et al. | |
| 4,872,459 A | 10/1989 | Pless et al. | |
| 4,880,005 A | 11/1989 | Pless et al. | |
| 4,928,688 A | 5/1990 | Mower | |
| 5,003,975 A | 4/1991 | Hafelfinger et al. | |
| 5,058,605 A | 10/1991 | Slovak | |

(Continued)

FOREIGN PATENT DOCUMENTS

EP    0522693    1/1993

(Continued)

OTHER PUBLICATIONS

Braunwald, Nina S., et al., "Sustained Paired Electrical Stimuli; Slowing of the Ventricular Rate and Augmentation of Contractile Force", *American Journal of Cardiology*, 14, (1964),pp. 285 & 385-393.

(Continued)

*Primary Examiner*—George Manuel
(74) *Attorney, Agent, or Firm*—Schwegman, Lundberg & Woessner, P.A.

(57) ABSTRACT

A cardiac rhythm management device in which amplitudes of electrograms from one or more cardiac sites are measured in order to ascertain the extent of hypertrophy. The device may then pace the heart by delivering pacing therapy in a manner that unloads the hypertrophied myocardium to effect reversal of undesirable remodeling.

18 Claims, 2 Drawing Sheets

U.S. PATENT DOCUMENTS

| | | |
|---|---|---|
| 5,156,149 A | 10/1992 | Hudrlik |
| 5,174,289 A | 12/1992 | Cohen |
| 5,233,985 A | 8/1993 | Hudrlik |
| 5,267,560 A | 12/1993 | Cohen |
| 5,340,361 A | 8/1994 | Sholder |
| 5,370,665 A | 12/1994 | Hudrlik |
| 5,507,782 A | 4/1996 | Kieval et al. |
| 5,514,161 A | 5/1996 | Limousin |
| 5,534,016 A | 7/1996 | Boute |
| 5,584,867 A | 12/1996 | Limousin et al. |
| 5,674,259 A | 10/1997 | Gray |
| 5,738,096 A | 4/1998 | Ben-Haim |
| 5,749,906 A | 5/1998 | Kieval et al. |
| 5,792,203 A | 8/1998 | Schroeppel |
| 5,797,970 A | 8/1998 | Pouvreau |
| 5,800,464 A | 9/1998 | Kieval |
| 5,824,019 A | 10/1998 | Rueter et al. |
| 5,935,160 A | 8/1999 | Auricchio et al. |
| 5,995,870 A | 11/1999 | Cazeau et al. |
| 5,995,871 A | 11/1999 | Knisley |
| 6,038,483 A | 3/2000 | KenKnight et al. |
| 6,058,329 A | 5/2000 | Salo et al. |
| 6,066,094 A | 5/2000 | Ben-Haim |
| 6,112,116 A * | 8/2000 | Fischell et al. .............. 600/517 |
| 6,112,117 A | 8/2000 | KenKnight et al. |
| 6,151,524 A | 11/2000 | Krig et al. |
| 6,223,082 B1 | 4/2001 | Bakels et al. |
| 6,285,898 B1 | 9/2001 | Ben-Haim |
| 6,292,693 B1 | 9/2001 | Darvish et al. |
| 6,314,322 B1 | 11/2001 | Rosenberg |
| 6,317,631 B1 | 11/2001 | Ben-Haim et al. |
| 6,363,279 B1 | 3/2002 | Ben-Haim et al. |
| 6,418,343 B1 | 7/2002 | Zhang et al. |
| 6,507,756 B1 | 1/2003 | Heynen et al. |
| 6,556,872 B2 | 4/2003 | Hauck |
| 6,628,988 B2 | 9/2003 | Kramer et al. |
| 6,640,135 B1 | 10/2003 | Salo et al. |
| 6,868,287 B1 | 3/2005 | Rosen et al. |
| 6,915,160 B2 | 7/2005 | Auricchio et al. |
| 6,965,797 B2 | 11/2005 | Pastore et al. |
| 6,973,349 B2 * | 12/2005 | Salo ............................. 607/11 |
| 7,065,405 B2 | 6/2006 | Pastore et al. |
| 7,103,410 B2 | 9/2006 | Kramer et al. |
| 7,158,824 B2 | 1/2007 | Girouard et al. |
| 7,215,997 B2 | 5/2007 | Yu et al. |
| 7,292,887 B2 | 11/2007 | Salo et al. |
| 7,295,874 B2 | 11/2007 | Prinzen et al. |
| 7,346,394 B2 | 3/2008 | Liu |
| 7,346,397 B2 | 3/2008 | Money et al. |
| 7,437,191 B2 | 10/2008 | Pastore et al. |
| 2002/0002389 A1 | 1/2002 | Bradley et al. |
| 2002/0045809 A1 | 4/2002 | Ben-Haim |
| 2002/0082647 A1 | 6/2002 | Alferness et al. |
| 2002/0115081 A1 | 8/2002 | Lee et al. |
| 2003/0105493 A1 | 6/2003 | Salo et al. |
| 2004/0030357 A1 | 2/2004 | Salo et al. |
| 2004/0044374 A1 | 3/2004 | Weinberg et al. |
| 2004/0049236 A1 | 3/2004 | Kramer et al. |
| 2004/0054381 A1 | 3/2004 | Pastore et al. |
| 2005/0065568 A1 | 3/2005 | Liu et al. |
| 2005/0177195 A1 | 8/2005 | Salo |
| 2006/0293716 A1 | 12/2006 | Kramer et al. |
| 2008/0097538 A1 | 4/2008 | Salo et al. |
| 2008/0097541 A1 | 4/2008 | Salo et al. |

FOREIGN PATENT DOCUMENTS

| | | |
|---|---|---|
| WO | WO-97/25098 | 7/1997 |
| WO | WO-9725098 A1 | 7/1997 |
| WO | WO-99/10042 | 3/1999 |
| WO | WO-00/04947 | 2/2000 |
| WO | WO-00/09206 | 2/2000 |
| WO | WO-2000/004947 A2 | 2/2000 |
| WO | WO-0004947 A2 | 2/2000 |
| WO | WO-01/08748 | 2/2001 |
| WO | WO-0108748 A2 | 2/2001 |
| WO | WO-01/30436 | 5/2001 |
| WO | WO-0130436 A2 | 5/2001 |
| WO | WO-01/76689 | 10/2001 |
| WO | WO-02/087694 | 11/2002 |

OTHER PUBLICATIONS

Sabbah, Hani N., et al., "Delivery of Non-Excitatory Contractility-Modulation Electric Signals Improve Left Ventricular Performance in Dogs with Heart Failure", *Circulation*, Supplement 1, 100 (18), Abstract No. 631,(Nov. 2, 1999),pp. I-122.

Watanabe, Michiko, et al., "Developmental Remodeling and Shortening of Cardiac Outflow Tract Involves Myocyte Programmed Cell Death", *Development*, 125 (19), (1998),3809-3820.

Schaldach, M., "Electrotherapy of the Heart", *Springer-Verlag*, (1992), 7,45,105.

\* cited by examiner

DYNAMICALLY OPTIMIZED MULTISITE CARDIAC RESYNCHRONIZATION DEVICE

CROSS-REFERENCE TO RELATED APPLICATION

This application is a continuation of U.S. patent application Ser. No. 10/071,875, filed on Feb. 8, 2002, now U.S. Pat. No. 6,915,160, the specification of which is incorporated herein by reference.

FIELD OF THE INVENTION

This invention pertains to cardiac rhythm management devices such as pacemakers and implantable monitoring devices.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. Other conduction defects can occur in the atria. Cardiac rhythm management devices have therefore been developed which provide electrical stimulation to the atria and/or ventricles in an attempt to improve the coordination of cardiac contractions, termed cardiac resynchronization therapy.

SUMMARY

The present invention relates to a method and apparatus for optimally delivering cardiac resynchronization therapy. Hypertrophied regions of the myocardium are identified by placing electrodes at selected myocardial regions and measuring the amplitudes of electrograms from the electrodes during depolarization events. Resynchronization pacing may then be delivered in a manner that pre-excites one or more of the hypertrophied regions in order to subject the region to a lessened preload and afterload. For example, the ventricles may be paced at a selected single electrode site using a conventional bradycardia pacing mode where the paced site is a region identified as hypertrophied. Alternatively, the ventricles may be paced at multiple sites using a multi-site resynchronization pacing mode, where the delivery of paces to multiple ventricular sites during a cardiac cycle is used to not only enforce a minimum ventricular heart rate but also to alter the depolarization patterns of the ventricles during systole and improve the coordination of the ventricular contraction. Multi-site ventricular resynchronization pacing may involve pacing both ventricles or only one ventricle at multiple sites by delivering a pacing pulse to each of the individual electrodes making up a pacing configuration in a specified pulse output sequence. The pulse output sequence can be specified so that one or more hypertrophied regions are paced before other regions during systole and hence mechanically unloaded. By unloading such hypertrophied regions in this way over a period of time, reversal of undesirable ventricular remodeling is effected. Pacing parameters also may be adjusted to increase the frequency of paced beats so that the hypertrophied region is unloaded more often.

In one particular embodiment of the invention, an implantable pacemaker is configured with sensing/pacing electrodes at a plurality of ventricular locations together with associated sensing and pacing channels for sensing intrinsic cardiac activity and delivering pacing pulses. By measuring the amplitudes of the individual electrogram signals generated at the multiple electrodes during depolarization events, areas of the ventricular myocardium in proximity to an electrode that are hypertrophied can be identified. Pacing may then be delivered through one or more selected electrodes in a manner such that a hypertrophied region of the myocardium is pre-excited relative to other regions during systole.

DETAILED DESCRIPTION

Applying cardiac resynchronization therapy in the most efficacious manner requires optimal selection of one or more pacing sites for the placement of pacing electrodes and, in the case of multi-site resynchronization pacing, the sequence in which pacing pulses should be output to the multiple pacing sites. One way of selecting a pacing site for resynchronization therapy is to measure the conduction delays of potential pacing sites during an intrinsic systolic contraction. One or more myocardial sites that are demonstrated to be excited later during an intrinsic contraction can then be selected as pacing sites. Pacing the late activated site, or pacing multiple sites in a sequence corresponding to their respective conduction delays, would then supposedly provide the desired resynchronization and a more coordinated contraction. Myocardial regions subjected to the highest levels of mechanical stress during intrinsic contractions, however, may not always be the latest activated regions due to the presence of scar tissue or areas of infarction. As is explained below, resynchronization pacing may be applied to such stressed myocardial regions in a manner that relieves the stress by reducing the preload and afterload to which the region is subjected. Such resynchronization pacing delivered over a period of time then causes reversal of undesirable myocardial remodeling.

In one of its aspects, the present invention provides a means by which a clinician may assess the extent to which particular myocardial regions have undergone hypertrophic remodeling due to increased mechanical stress. This information can then be used to select an optimum pacing configuration for delivering resynchronization pacing therapy in order to mechanically unload the hypertrophied regions. As the therapy is applied over time, the myocardium may undergo further changes due to disease progression or due to the beneficial effects of the resynchronization therapy or other therapies. The invention also allows for the design of a device that monitors these changes so that therapy adjustments can be made. In one embodiment, a pacemaker is equipped with multiple sensing and pacing channels and programmed to automatically re-configure itself in accordance with such changes.

1. Exemplary Device Description

Conventional cardiac pacing with implanted pacemakers involves excitatory electrical stimulation of the heart by the delivery of pacing pulses to an electrode in electrical contact with the myocardium. The pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 1:
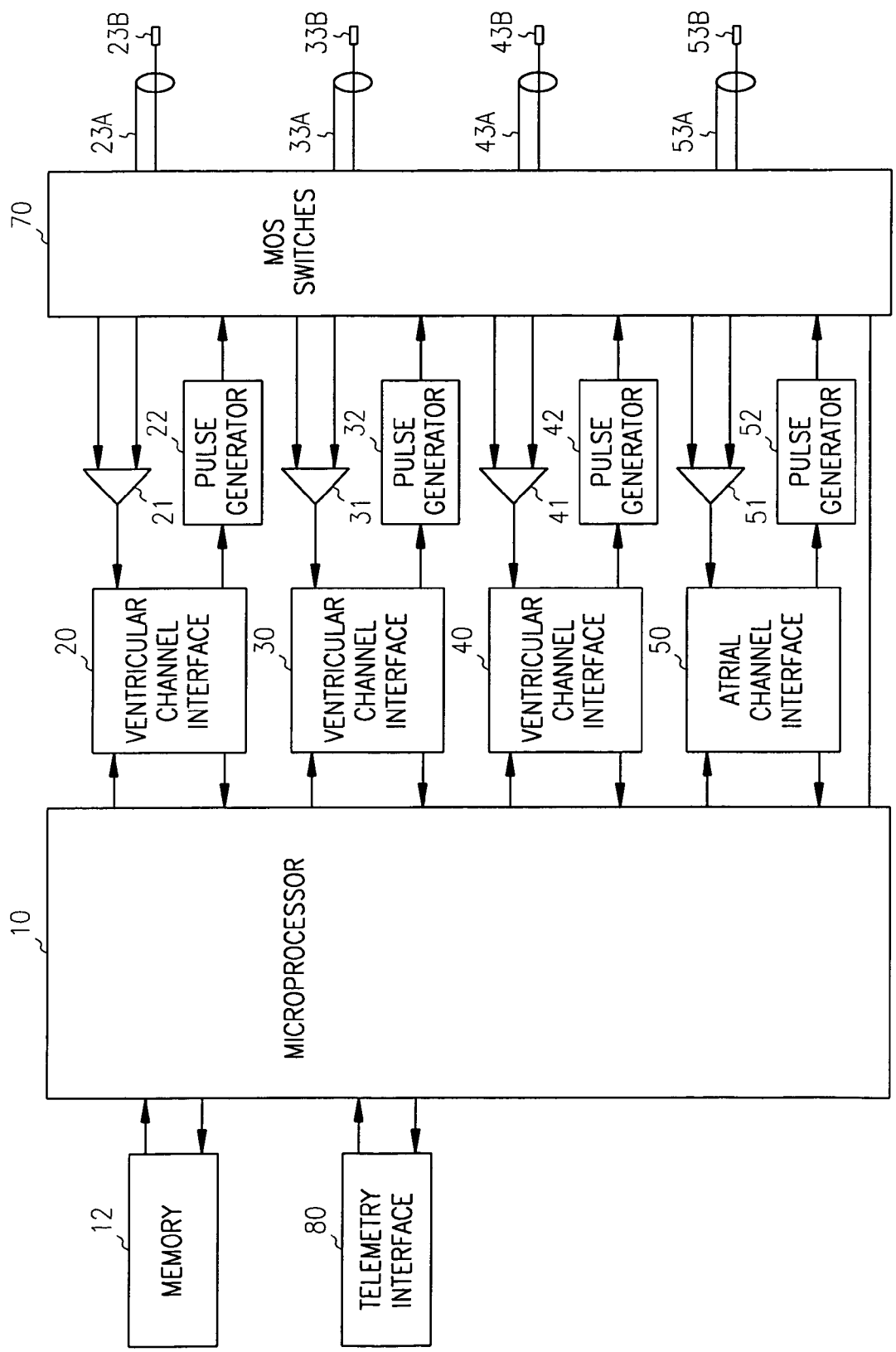
FIG. 1 is a block diagram of an exemplary cardiac rhythm management device for practicing the present invention.

A block diagram of a multi-site pacemaker having multiple sensing and pacing channels is shown in FIG. 1. (As the term is used herein, a "pacemaker" should be taken to mean any cardiac rhythm management device, such as an implantable cardioverter/defibrillator, with a pacing functionality). The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is also provided for communicating with an external programmer.

The multiple sensing and pacing channels of the device in FIG. 1 may be configured as either atrial or ventricular channels allowing the device to deliver conventional ventricular single-site pacing with or without atrial tracking, biventricular pacing, or multi-site pacing of a single chamber. Shown in FIG. 1 is a configuration with one atrial sensing/pacing channel and three ventricular sensing/pacing channels. The atrial sensing/pacing channel in FIG. 1 comprises ring electrode 53a, tip electrode 53b, sense amplifier 51, pulse generator 52, and an atrial channel interface 50 which communicates bidirectionally with a port of microprocessor 10. The three ventricular sensing/pacing channels that include ring electrodes 23a, 33a, and 43a, tip electrodes 23b, 33b, and 43b, sense amplifiers 21, 31, and 41, pulse generators 22, 32, and 42, and ventricular channel interfaces 20, 30, and 40. A pacing channel is made up of the pulse generator connected to the electrode while a sensing channel is made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. For each channel, the same electrode pair is used for both sensing and pacing. In this embodiment, bipolar leads that include two electrodes are used for outputting a pacing pulse and/or sensing intrinsic activity. Other embodiments may employ a single electrode for sensing and pacing in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory. The controller 10 interprets electrogram signals from the sensing channels and controls the delivery of paces in accordance with a pacing mode. The sensing circuitry of the pacemaker generates atrial and ventricular electrogram signals from the voltages sensed by the electrodes of a particular channel. When an electrogram signal in an atrial or sensing channel exceeds a specified threshold, the controller detects an atrial or ventricular sense, respectively, which pacing algorithms may employ to trigger or inhibit pacing. An electrogram is analogous to a surface ECG and indicates the time course and amplitude of cardiac depolarization that occurs during either an intrinsic or paced beat. As described below, measurement of the amplitudes of electrogram R waves from the different sensing channels allows the device to ascertain regions of relative hypertrophy in the myocardium.

2. Bradycardia Pacing Modes

Bradycardia pacing modes refer to pacing algorithms used to pace the atria and/or ventricles in a manner that enforces a certain minimum heart rate. Such modes are generally designated by a letter code of three positions where each letter in the code refers to a specific function of the pacemaker. Pacemakers can enforce a minimum heart rate either asynchronously or synchronously. In asynchronous pacing, the heart is paced at a fixed rate irrespective of intrinsic cardiac activity. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In an atrial tracking pacing mode (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body. A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

3. Resynchronization Pacing Modes

Cardiac resynchronization therapy is pacing stimulation applied to one or more heart chambers in a manner that restores or maintains synchronized contractions of the atria and/or ventricles and thereby improves pumping efficiency. Ventricular resynchronization pacing is useful in treating heart failure in patients with interventricular or intraventricular conduction defects because, although not directly ionotropic, resynchronization results in a more coordinated contraction of the ventricles with improved pumping efficiency and increased cardiac output. Resynchronization pacing of the atria may also be beneficial in certain patients, particularly for preventing the onset of atrial arrhythmias.

Certain patients with conduction abnormalities may experience improved cardiac synchronization with conventional single-chamber or dual-chamber bradycardia pacing as described above because of the way in which depolarization is spread as a result of a pace as opposed to an intrinsic contraction. Resynchronization pacing, however, may also involve delivering paces to multiple sites of either the atria or the ventricles during a cardiac cycle. The multiple pacing sites may be located in a single heart chamber or in both ventricles or both atria. In multi-site pacing, the atria or ventricles are paced at more than one site in order to effect a spread of excitation that results in a more coordinated contraction. Biventricular resynchonization pacing is one example of multi-site pacing in which both ventricles are paced in order to synchronize their respective contractions. Biventricular resynchronization pacing may be useful in treating certain conduction pathologies such as bundle branch blocks. Multi-site pacing may also be applied to only one chamber. For example, a ventricle may be paced at multiple sites with excitatory stimulation pulses in order to produce multiple waves of depolarization that emanate from the pacing sites. This may produce a more coordinated contraction of the ventricle and thereby compensate for intraventricular conduction defects that may exist.

One way to deliver multi-site resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. For example, in an offset resynchronization pacing mode, a primary pacing site is paced with a bradycardia mode, and one or more secondary sites are then paced at specified offset intervals with respect to the pace delivered to the primary site. An offset interval may be zero in order to pace both sites simultaneously, positive in order to pace the primary site after the secondary site, or negative to pace the primary site before the secondary site.

4. Heart Failure and Myocardial Remodeling

Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as myocardial remodeling. Hypertrophy can increase systolic pressures but also decreases the compliance of the ventricles and hence increases diastolic filling pressure to result in even more congestion. It also has been shown that the sustained stresses causing hypertrophy may induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the process ultimately results in both systolic and diastolic dysfunction. It has been shown that the extent of ventricular remodeling is positively correlated with increased mortality in heart failure patients.

The degree to which a heart muscle fiber is stretched before it contracts is termed the preload, while the degree of tension or stress on a heart muscle fiber as it contracts is termed the afterload. The maximum tension and velocity of shortening of a muscle fiber increases with increasing preload, and the increase in contractile response of the heart with increasing preload is known as the Frank-Starling principle. When a myocardial region contracts late relative to other regions, the contraction of those other regions stretches the later contracting region and increases its preloading, thus causing an increase in the contractile force generated by the region. Because pressure within the ventricles rises rapidly from a diastolic to a systolic value as blood is pumped out into the aorta and pulmonary arteries, the parts of the ventricles that contract later during systole do so against a higher afterload than do parts of the ventricles contracting earlier. Thus a ventricular region that contracts later than other regions is subjected to both an increased preload and afterload, both of which act to increase the mechanical stress experienced by the region relative to other regions. This situation is created frequently by the ventricular conduction delays associated with heart failure and ventricular dysfunction. The heart's initial physiological response to the uneven stress resulting from an increased preload and afterload is compensatory hypertrophy in those later contracting regions of the ventricular myocardium. In the later stages of remodeling, the regions may undergo atrophic changes with wall thinning due to continuing of the increased stress.

5. Reversal of Remodeling with Resynchronization Therapy

The parts of the myocardium that contract earlier in the cycle, on the other hand, are subjected to less stress and are less likely to undergo hypertrophic remodeling. This phenomena can be used for effecting reversal of remodeling by delivering paces to one or more ventricular pacing sites in a manner that pre-excites one or more hypertrophied region. In a normal heartbeat, the specialized His-Purkinje conduction network of the heart rapidly conducts excitatory impulses from the sino-atrial node to the atrio-ventricular node, and thence to the ventricular myocardium to result in a coordinated contraction of both ventricles. Artificial pacing with an electrode fixed into an area of the myocardium does not take advantage of the heart's normal specialized conduction system for conducting excitation throughout the ventricles because the specialized conduction system can only be entered by impulses emanating from the atrio-ventricular node. Thus the spread of excitation from a ventricular pacing site must proceed only via the much slower conducting ventricular muscle fibers, resulting in the part of the ventricular myocardium stimulated by the pacing electrode contracting well before parts of the ventricle located more distally to the electrode.

The pre-excitation of a paced site relative to other sites can be used to deliberately change the distribution of wall stress experienced by the ventricle during the cardiac pumping cycle. Such pre-excitation of a remodeled or hypertrophied region relative to other regions unloads the region from mechanical stress by decreasing its afterload and preload, thus allowing reversal of remodeling to occur. Pacing therapy to unload hypertrophied regions may be implemented by pacing the ventricles at a single site or by pacing at multiple ventricular sites where the pulse output sequence to the different electrodes is such that one or more regions are excited earlier than the rest of the myocardium. Paces may be delivered in accordance with an inhibited demand mode or a triggered mode. In the latter case, one or more pre-excitation pacing pulses are applied to a hypertrophied region immediately following the earliest detection of intrinsic activation elsewhere in the ventricle.

6. Identification of Hypertrophied Regions and Optimization of Resynchronization Pacing A wave of depolarization propagating through a hypertrophied myocardial region results in a greater potential being measured by a sensing electrode owing to the greater muscle mass. During a depolarization event (i.e., either an intrinsic or paced beat), an electrogram signal measured from an internal electrode disposed near a relatively hypertrophied region in the heart is therefore of greater amplitude than a signal measured from an electrode near an unhypertrophied region. This phenomena can be used to identify areas of hypertrophy by measuring the amplitudes of electrograms from electrodes placed at locations so as to sense different regions of the myocardium. A pacemaker can then be configured to deliver pacing therapy that pre-excites the region or regions so identified. For example, a pacemaker may be configured to deliver single-site bradycardia pacing to the ventricles where an identified hypertrophic region is selected as the pacing site. A pacemaker may also be configured to deliver multi-site resynchronization pacing to a plurality of pacing sites with a pulse output sequence that specifies the order of the paces to correspond to the regional assessment of myocardial hypertrophy. For example, the pulse output sequence may specify that pacing pulses are delivered to more hypertrophied regions before less hypertrophied or normal regions.

As illustrated in FIG. 1, a pacemaker may also be equipped with multiple electrodes for disposition at multiple sites where the electrodes are incorporated into sensing channels that allow an electrogram signal to be generated from each individual electrode. By measuring the amplitudes of the electrograms from the multiple electrodes during systole (i.e., the amplitude of an R wave in the case of a ventricular electrogram), the extent of hypertrophy at each of the electrode sites can be assessed. This information can then be used to select one or more of the available electrodes for delivering pacing pulses to the heart in a manner that redistributes stress during systole and causes reversal of the hypertrophy. The pacemaker may also be programmed to periodically measure and compare the R wave amplitudes from the multiple electrodes in order to monitor changes in the myocardium over time, and trending of the R wave amplitudes may be performed in order to predict future changes. The pacemaker may also be programmed to automatically re-configure itself to deliver resynchronization pacing therapy that pre-excites the stressed regions determined by the measured R wave amplitudes. The pacemaker controller can thus be programmed to select an optimum pacing configuration that defines which of the available implanted electrodes are to be used for pacing and, in the case of multi-site pacing, be further programmed to select a pulse output sequence that specifies the optimum order of the pacing pulses.

Figure 2:
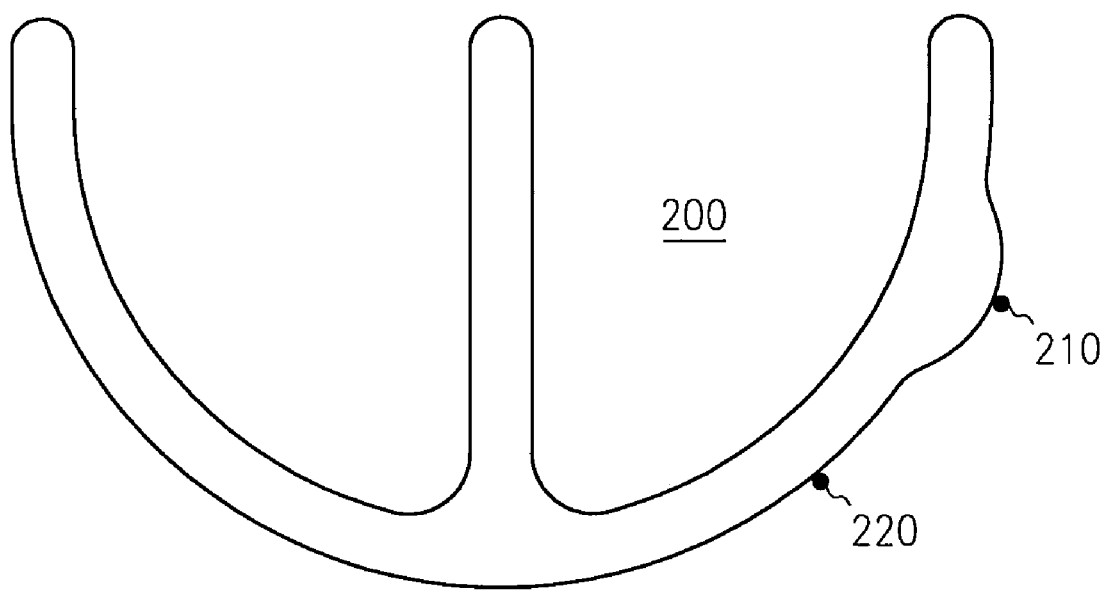
FIG. 2 shows an exemplary placement of sensing/pacing electrodes.

FIG. 2 depicts an example situation where the left ventricle 200 has epicardial pacing/sensing electrodes disposed at pacing sites 210 and 220. Placement of such electrodes may be accomplished transvenously via the coronary sinus. The myocardium at pacing site 210 is shown as being hypertrophied as compared to the myocardium at pacing site 220 as a result of being subjected to greater stress. A pacemaker such as illustrated in FIG. 1 may incorporate the two electrodes into sensing and pacing channels. By measuring the amplitudes of the electrogram R waves from the two sites, it may be determined that the site 210 is hypertrophied. The pacemaker may then be configured to deliver biventricular pacing with a pulse output sequence specifying that site 210 is paced before site 220.

The device of FIG. 1 may be further programmed to automatically adjust the pacing parameters for a given pacing configuration and pulse output sequence in accordance with periodic regional assessments of hypertrophy. For example, if it is determined that regional hypertrophy has increased more than expected, parameters may be adjusted that increase the delay between pre-excitation of the hypertrophied region and excitation of less hypertrophied or normal regions. Conversely, if some of the desired reversal of remodeling has occurred, so that a pre-excited region has become less hypertrophied, the degree of pre-excitation relative to other regions may be decreased by decreasing the delay. Parameters that determine the frequency of pacing may also be adjusted in accordance with periodic regional assessments of hypertrophy. Pacing frequency may be increased by, for example, increasing the LRL and/or decreasing the atrio-ventricular interval. As it is only paced beats that unload the hypertrophied regions, more frequent pacing increases the therapeutic benefit of the therapy in reversing remodeling. It may be desirable, therefore, to increase or decrease the pacing frequency in accordance with the assessment of hypertrophy.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac device, comprising:
   a plurality of electrodes for disposition near different myocardial regions, wherein each such electrode may be connected to a pulse generator for delivering a pacing pulse and may be connected to a sense amplifier for generating an electrogram signal;

a controller programmed to deliver pacing pulses through one or more electrodes in accordance with a programmed pacing mode;

wherein the controller is programmed to measure the amplitudes of R waves of electrograms generated by the plurality of electrodes during a depolarization event and configure one or more pacing channels with electrodes selected in accordance with the measured amplitudes.

2. The device of claim 1 wherein the controller is programmed to deliver pacing pulses in a manner that pre-excites the myocardial region with the largest measured electrogram amplitude relative to other myocardial regions.

3. The device of claim 2 wherein the controller is programmed to deliver multi-site resynchronization pacing with a pacing configuration and pulse output sequence that specifies the order of the pacing pulses delivered to the different myocardial regions in accordance with the amplitudes of the measured electrograms.

4. The device of claim 2 wherein the controller is programmed to periodically measure electrogram amplitudes and automatically reconfigure itself to deliver pacing therapy with a pacing configuration that pre-excites a myocardial region with the largest electrogram amplitude.

5. The device of claim 4 wherein the controller is programmed to periodically measure electrogram amplitudes and automatically reconfigure itself to deliver multi-site resynchronization pacing with a pacing configuration and pulse output sequence that specifies the order of the pacing pulses delivered to the different myocardial regions in accordance with the amplitudes of the electrograms.

6. The device of claim 4 wherein the controller is programmed to adjust a pacing parameter that increases the frequency of pacing if it is determined that the electrogram amplitude has increased.

7. The device of claim 4 wherein the controller is programmed to adjust a pacing parameter that increases the delay between pre-excitation of a hypertrophied myocardial region and excitation of other regions if it is determined that the electrogram amplitude has increased.

8. The device of claim 4 wherein the controller is programmed to adjust a pacing parameter that decreases the delay between pre-excitation of a hypertrophied myocardial region and excitation of other regions if it is determined that the electrogram amplitude has decreased.

9. The device of claim 1 wherein the controller is programmed to compute a trend for the measured electrogram amplitudes.

10. A method, comprising:
    implanting a multi-site pacing device with electrodes disposed at a plurality of myocardial sites;
    measuring the amplitudes of R waves of electrograms generated at the plurality of myocardial sites during a depolarization event and comparing the measured amplitudes;
    configuring the pacing channels of the multi-site pacing device to deliver pacing therapy in accordance with a programmed pacing mode that pre-excites the myocardial site with the largest R wave amplitude.

11. The method of claim 10 further comprising adjusting a pacing parameter that determines the delay between pre-excitation of a myocardial site and excitation of other myocardial sites in accordance with the measured electrogram amplitude.

12. The method of claim 10 further comprising disposing pacing electrodes at a plurality of myocardial sites and delivering multi-site pacing therapy in accordance with a programmed pacing mode and with a pacing configuration that specifies the order of the pacing pulses delivered to the different myocardial sites in accordance with their measured electrogram amplitudes.

13. A method for operating a cardiac device, comprising:
    delivering pacing pulses through one or more electrodes in accordance with a programmed pacing mode and pacing configuration;
    measuring the amplitudes of R waves of electrograms generated by a plurality of electrodes disposed near a plurality of myocardial regions during a depolarization event and comparing the measured amplitudes;
    adjusting the pacing mode and/or pacing configuration to deliver pacing pulses in a manner that pre-excites the myocardial region with the largest measured R wave amplitude relative to other myocardial regions;
    periodically measuring electrogram amplitudes and reconfiguring the device to deliver pacing therapy with a pacing configuration that pre-excites a myocardial region with the largest electrogram amplitude; and,
    adjusting a pacing parameter that increases the delay between pre-excitation of a hypertrophied myocardial region and excitation of other regions if it is determined that the electrogram amplitude has increased.

14. The method of claim 13 further comprising delivering multi-site resynchronization pacing with a pacing configuration and pulse output sequence that specifies the order of the pacing pulses delivered to the different myocardial regions in accordance with the amplitudes of the measured electrograms.

15. The method of claim 13 further comprising periodically measuring electrogram amplitudes and reconfiguring the device to deliver multi-site resynchronization pacing with a pacing configuration and pulse output sequence that specifies the order of the pacing pulses delivered to the different myocardial regions in accordance with the amplitudes of the electrograms.

16. The method of claim 13 further comprising adjusting a pacing parameter that increases the frequency of pacing if it is determined that the electrogram amplitude has increased.

17. The method of claim 13 further comprising adjusting a pacing parameter that decreases the delay between pre-excitation of a hypertrophied myocardial region and excitation of other regions if it is determined that the electrogram amplitude has decreased.

18. The method of claim 13 further comprising computing a trend for the measured electrogram amplitudes.

* * * * *